United States Patent [19]
Ueno

[11] Patent Number: 5,513,984
[45] Date of Patent: May 7, 1996

[54] SPACER AND MOUTHPIECE FOR ADJUSTING OCCLUSION

[75] Inventor: Masato Ueno, Hiroshima, Japan

[73] Assignees: Molten Corporation; Chugoku Shiken Kabushiki Kaisha, both of Hiroshima, Japan

[21] Appl. No.: 376,650

[22] Filed: Jan. 20, 1995

Related U.S. Application Data

[63] Continuation of Ser. No. 120,550, Sep. 14, 1993, abandoned, which is a continuation of Ser. No. 942,454, Sep. 9, 1992, Pat. No. 5,299,936.

[30] Foreign Application Priority Data

Sep. 20, 1991 [JP] Japan .................................. 3-084939
Dec. 11, 1991 [JP] Japan .................................. 3-109858
Jan. 18, 1992 [JP] Japan .................................. 4-005731

[51] Int. Cl.$^6$ ..................................................... A61C 3/00
[52] U.S. Cl. ............................................... 433/6; 128/861
[58] Field of Search .......................... 433/6, 71; 128/861, 128/862

[56] References Cited

U.S. PATENT DOCUMENTS

| | | | |
|---|---|---|---|
| 3,089,487 | 5/1963 | Enicks | 128/861 |
| 3,211,143 | 10/1965 | Grossberg | 128/862 |
| 4,472,140 | 9/1984 | Lustig | 433/38 |
| 4,541,803 | 9/1985 | Adler | 433/141 |
| 5,031,638 | 6/1991 | Casialdi | 128/861 |

*Primary Examiner*—Nicholas D. Lucchesi
*Attorney, Agent, or Firm*—Armstrong, Westerman, Hattori, McLeland & Naughton

[57] ABSTRACT

A spacer for elevating occlusion position is composed of a plastic material which can be deformed by occlusion pressure; and a plurality of ball members having a predetermined diameter. The ball member is made of a material which cannot be deformed by subjecting occlusion pressure, and the ball member is embedded in the plastic material so as to be in a plane.

5 Claims, 9 Drawing Sheets

SPACER AND MOUTHPIECE FOR ADJUSTING OCCLUSION

This application is a continuation application of application Ser. No. 08/120,550, filed Sep. 14, 1993, now abandoned which is a continuation of application Ser. No. 07/942,454, filed Sep. 9, 1992, now U.S. Pat. No. 5,299,936.

BACKGROUND OF THE INVENTION

The present invention relates to a spacer which is located between upper and lower molars and enables to keep a predetermined space, for adjusting occlusion, and a mouthpiece which are mounted on teeth located in an upper or a lower jaw by using a spacer.

When a denture or a mouthpiece available for athletic sports is produced, in many cases a wax plate having a thickness of 3 to 4 mm (which is called a bite wax) has hitherto been used. The bite wax is bitten in a state, wherein the bite wax is softened by heating, by a patient or the like so that a dell is formed on both sides thereof. Thereby, a mutual relationship of the upper and the lower jaw in such a state that the elevation of several mm as to the occlusion is obtained. On the other hand, a gnathic model, which is made from gypsum, of patients and the like is formed. Thereafter, the model is inserted into an articulator in such a manner that the bite wax is interposed between the upper and the lower molar parts the model. Thereby, the mutual relationship, wherein the elevation having a predetermined space is performed, is reproduced. Thereby, producing the denture or the mouthpiece is performed.

When the elevation of the position of occlusion is performed by using the bite wax as mentioned hereinbefore, the space of the elevation varies in accordance with occlusion pressure (high pressure or low pressure). For this reason, considerable maturity is required even for a dentist in order to obtain a predetermined value of elevation. As is often the case, the value of elevation is still thinner or thicker than the desired value of elevation. Then, it is quite often that the patient bites off the bite wax.

With respect to the mouthpiece which is put on sale (or available), a player (or athlete) buys the bite wax in a shop, and thereafter soaks it in hot water. Thereby, the bite wax is softened. Then, the mouthpiece is shaped by biting between the upper and the lower molars, and pressure is applied to the mouthpiece from tongue-side and cheek-side. However, in the above case, it is very difficult to obtain an optimum value, which is set beforehand, of the elevation of the position of occlusion. It depends upon a temperature of the hot water and soaking time that material of the mouthpiece softens. Further, there is a difference between individuals in the occlusion pressure. For this reason, it often happens that the space of elevation is thicker or thinner than the standard value and the above-mentioned problems arise.

As this kind of the mouthpiece, the mouthpiece made of a thermoplastic resin which is softened at a temperature being not more than 100° C. having such a construction as to be inserted by the core member such as a weaving cloth is known (Japanese Unexamined Patent Publication No. 60672/1990).

Further, the above Japanese Publication discloses a mouthpiece wherein softened resin is prevented from dropping down by the core member when the mouthpiece is heated. The above Japanese Publication does not disclose such a technique that the position of occlusion is elevated with a certain space between the upper and the lower molar by means of the core member. Actually, weaving cloth or woven fabric is so thin that the elevation of the position of occlusion cannot be performed by several nun. Then, if the weaving cloth and the like is made to be thick so as to have a thickness of several mm, restoring force against deformation is so big as to be ignored since elastic modulus of the weaving cloth is higher than that of the above thermoplastic resin. As a result, the mouthpiece is in danger of deforming before the mouthpiece is cured by cooling after shaping.

The object of the present invention is to delete the above problems and to provide a spacer and a mouthpiece, wherein an elevation of position of occlusion with having a predetermined space between the upper and the lower molars, can be easily and accurately performed by even a person who is not mature.

SUMMARY OF THE INVENTION

In accordance with the present invention, there is provided with a spacer for elevating occlusion position comprising: a plastic material which can be deformed by occlusion pressure; and a plurality of ball members having a predetermined diameter; said ball members being made of a material which cannot be deformed by applying occlusion pressure, and said ball members being embedded in the plastic material so as to be in a plane. The ball members can be connected by joint members having a flexibility. Further, diameter of the ball members can be set in a range from 0.3 to 6.0 min. Further, the ball members can be formed by a thermoplastic elastomer having a softening point which is higher than 100° C. Further, the plastic material can be formed by a wax or a thermoplastic elastomer having a softening point which is higher than 50° C.

Furthermore, the mouthpiece of the present invention comprises the spacer for elevating occlusion position which is embedded in the mouthpiece, and the plastic material is made of thermoplastic elastomer having a softening point being not less than 50° C., and the mouthpiece is formed into a horseshoe shape which is accorded with dentition having arc like shape and provided with a skirt extending in the side of the tongue and a side of the cheek.

Furthermore, the other mouthpiece of the present invention comprises a mouthpiece body being made of a thermoplastic elastomer having a softening point which is in a range of 50° to 100° C.; and an elevating member for elevating occlusion position with a predetermined space; said mouthpiece body being formed into a horseshoe like shape so as to accord with dentition having arc like shape; characterized in that said elevating member having a softening point which is higher than 100° C., and being made of a string like member having a hardness which is substantially the same as that of said mouthpiece body at a temperature of 37° C. The spacer for elevating occlusion position is inserted into a mouth and interposed between an upper molar and a lower molar in the state that the plastic material softened by heating, thereafter the spacer is slowly bitten by the molars. Then, when a patient and the like feels the resistance, the patient and the like stops to bite the spacer, then the spacer is took out. Thus, on both sides of the spacer, impressions in an occlusion surface between molars on both upper and lower jaw are formed and spaced by the ball member.

With respect to the mouthpiece, the mouthpiece is softened by soaking in the hot water or the like, thereafter inserted into the mouth and bitten by the upper and lower molars, at the same time the skirt located in the tongue side is pushed by the tongue and the skirt located in the cheek side is pushed by a finger or the like, then the mouthpiece is shaped so as to be elevated with a certain space.

DETAILED DESCRIPTION

Figure 1:
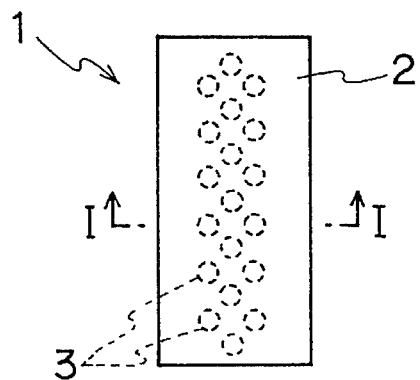
FIG. 1 is a plan view showing an embodiment of a spacer for elevating occlusion position of the present invention.
Figure 2:
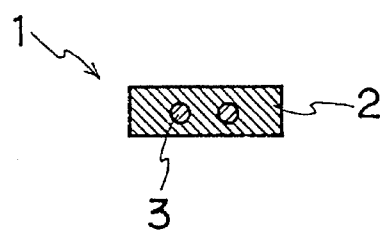
FIG. 2 is a sectional view along with the line I—I in FIG. 1.

In FIGS. 1 and 2, numeral 1 denotes a spacer for elevating an occlusion position comprising a sheet 2 which is about 40 mm by 15 mm, a thickness of which is about 3 mm, and which is made of a plastic material such as a thermoplastic elastomer (ethylene/vinyl acetate copolymer or the like), a thermoplastic resin (wax, polycaprolactam resin, gutta-percha or the like), self curing resin for dental use at normal temperature which is obtained by adding methyl methacrylate monomer liquid and polymerization initiator to polyethyl methacrylate (PEMA) resin powder, then kneading each other, impressing material for dental use such as alginic acid impressing material, silicone impressing material tissue treatment material which is obtained by mixing PEMA resin powder with plastic material such as butyl phthalyl butyl glycolate and ethanol, and a gypsum and the like; and a plurality of ball members 3, 3 which is embedded in the sheet 2, and is made of thermoplastic elastomer (thermoplastic elastomer olefin, styrene block copolymer, thermoplastic elastomer urethane or the like), a single body or composite of polyethylene resin, polypropylene resin, nylon resin, polyurethane resin, polystyrene resin, acrylonitrile-butadiene-styrene resin, acrylonitrilestrylene resin, polycarbonate resin, vinyl chloride resin, polyethylene terephthalate resin, polybuthyleneterephthalate resin, polymethyl methacrylate resin, polyethyl methacrylate resin, polyether sulphone resin, polyacetal resin, epoxy resin. Diameter of the ball member 3 is set to a certain value in a range from 0.3 to 6.0 mm in accordance with a use of the spacer. With respect to the mouthpiece for athletic use, a standard value of the diameter is about 2.0 min. The ball members 3 are uniformly arranged in a plane with a space of about 2 mm. When thermoplastic resin is used as a material of the sheet 2, softening point of the sheet 2 is in a range from normal temperature (about 20° C.) to about 80° C. For this reason, when the sheet 2 is soaked in the hot water, the sheet 2 is softened and deformed due to a pressure of occlusion. The self curing resin at normal temperature, the impressing material, the tissue treatment material and the gypsum are prepared by their peculiar method. Further, when the self curing resin is used as the material of the sheet 2, the sheet 2 can be used as a positioner for curing hyposiagonarthritis. On the other hand, the ball member 3 must be formed by the material which does not deform even if the ball member 3 is heated to about 20° to 80° C. Accordingly, the above thermoplastic elastomer and the like having softening point which is higher than 100° C., is used as the material of the ball member 3.

Figure 3:
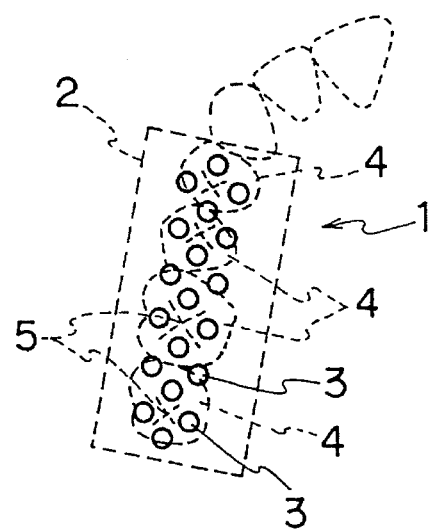
FIG. 3 is a plan view illustrating a relationship between a spacer for elevating occlusion position and a molar.
Figure 4:
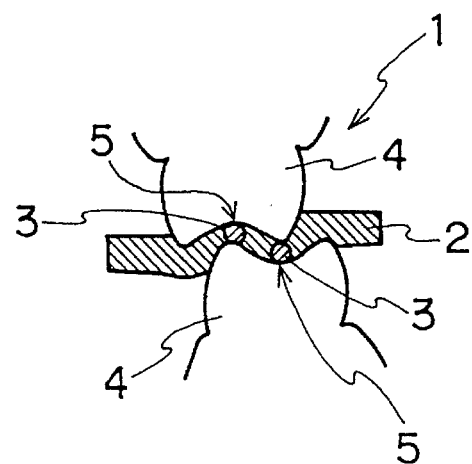
FIG. 4 is a sectional view illustrating an occlusion state.

The above-mentioned spacer 1 for elevating occlusion position is mounted on four molars 4 as shown in FIGS. 3 and 4, then the spacer is bitten. Besides, FIG. 3 the sheet 2 (shown in dashed line) is omitted. The sheet 2 is depressed due to a pressure of occlusion. The ball members 3 do not deform even if subjected to a pressure of occlusion. For this reason, the upper and the lower molars are spaced with a length determined by the diameter of the ball member. The reason why the ball members 3 are arranged in the sheet 2 so as to be in a plane is that when the ball members are not arranged in a plane and there is a possibility that they are deformed vertically, a predetermined elevation cannot be obtained since each of two or more ball members 3 is placed one above other in a fossa 5 of the molar 4.

Figure 5:
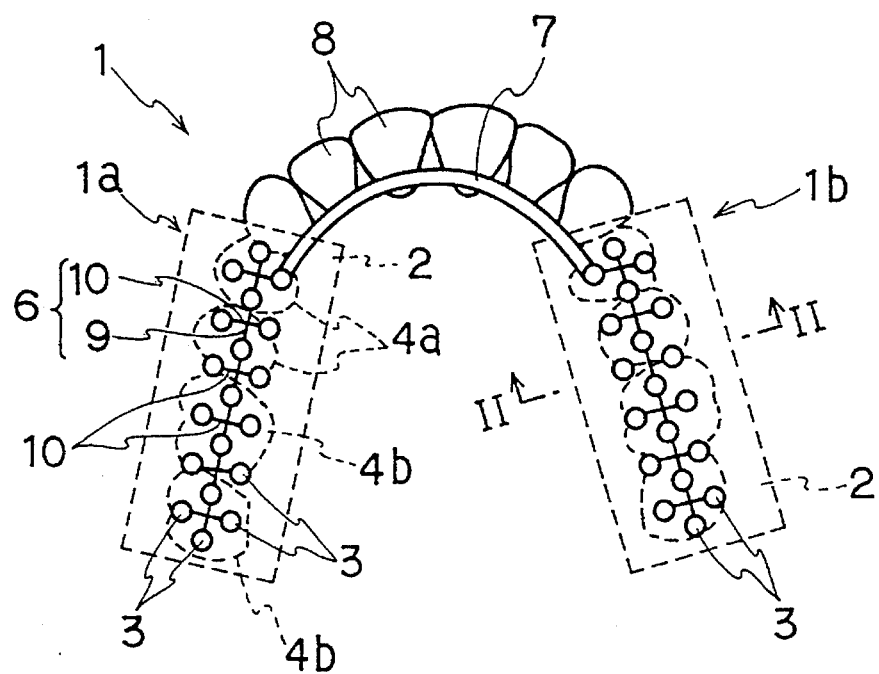
FIG. 5 plan view illustrating another embodiment of a spacer for elevating occlusion position of the present invention.
Figure 6:
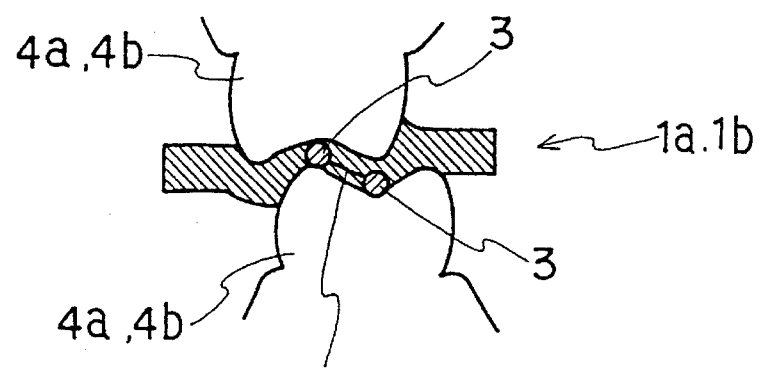
FIG. 6 is a sectional view along the line II—II in FIG. 5.

In order to surely prevent each of the ball members 3 from being placed one above the other, the construction wherein the ball members 3 are connected to each other by a joint member 6 having a string like shape may be employed as shown in FIGS. 5 and 6 illustrating an embodiment. In the embodiment, the spacer 1 for elevating occlusion position comprises spacer parts 1a, 1b and a connecting part 7 for connecting the spacer part 1a and the another spacer part 1b. The connecting part 7 is formed such that the connecting part 7 is located in the tongue side of the anterior tooth when the spacer 1 is inserted the mouth and the spacer parts 1a, 1b are interposed between the upper and the lower jaw. The spacers 1a, 1b are not necessarily combined each other, each of the spacers 1a, 1b may be used independently. Further, when the connecting part 7 is covered with wax, the shape of spacer 1 can be kept to be a horseshoe like shape. The joint member 6 comprises a main joint member 9 extending in the direction of dentition and a sub joint member 10 substantially perpendicular to the main joint members 9. Each of the main and the sub joint member 9, 10 is formed into a string like shape wherein the diameter thereof is in the range from 0.1 to 0.5 mm. A plurality of the ball members 3 having a diameter of about 2.0 mm is arranged in the in the spacers 1a, 1b so as to be connected by the main joint member 9 with a space of approximately 5 mm, and the sub joint member 10 is crossed with the sub joint member 9 at a right angle in the part thereof located between the ball members 3. The ball members 3 are disposed at both ends of the sub joint member 10. The length of the sub joint member 10 corresponding to a bicuspid 4a (a pitch between the ball members 3 located at both ends of the sub joint member 3) is about 4 mm. The length of the sub joint member 10 corresponding to the molar 4b (a pitch between the ball members 3 located at both ends of the sub joint member 3) is about 5 mm. With respect to the mouthpiece for athlete use, the diameter of the ball member 3 is usually in a range from about 1.0 to 3.0 mm in accordance with a kind of the athlete and objects of using the mouthpiece. The ball member having a diameter of 2.0 mm is standardly used as the description mentioned hereinbefore. With respect to the mouthpiece which is used for curing axis deviation of upper and lower jaw (malocclusion, or eccentric occlusion), which is called a template, a range of diameter is set at a value being in a range from 0.3 to 6.0 mm in accordance with case of the patients. When the occlusion position is elevated in producing a denture, the diameter is often set at the value being in a range from 0.5 to 1.0 mm. The ball member 3, the joint member 6 and the connecting part 7 are integrally formed by injection moulding or press moulding of the above resin material such as thermoplastic elastomer olefin. Numeral 2 denotes a sheet which defines the spacer 1a, 1b covering the ball members 3 and is made of plastic resin such as wax, polycaprolactam. The size of the sheet can be about 40 mm by 15 mm and thickness of the sheet can be about 3 mm, which is the same as the above-mentioned embodiment. Such a size is enough to cover four pieces of molars of adults. As the material of the ball members 3 and the joint member 6, thermoplastic resin having no elasticity can be used. Besides, it is desirable that the ball members 3 have length to cover the four molars. It is enough to dispose the sheet in the portion corresponding to the fifth and sixth teeth.

As shown in FIGS. 5 and 6, the spacer 1 for occlusion is bit in such a state that the space 1 is softened and adjusted to position and is approximately centered in the molar 4a, 4b, thereby the sheet 2 is deformed, the ball member 3 on the main joint member 9 is positioned at the fossa which is the center of the tooth, the ball member 3 on the sub joint member 10 is positioned respectively in the tongue side of cuspis and cheek side cuspis. The ball members 3 are connected each other by means of the joint member 6, thereby movement of the ball member is restricted. For this reason, the location of the ball members is not varied drastically and each of the ball members is not placed one above the other even if the sheet 2 is deformed and flowed by the occlusion pressure. Since the ball member 3 is not deformed by the occlusion pressure, the space between the upper and the lower molars 4a, 4b is accurately decided so as to accord with the diameter of the ball member 3. Besides, each of the main and sub joint members 9, 10 is thin and has flexibility. Accordingly, when the spacer 1 is applied to occlusion pressure, the main and the sub joint members 9, 10 are deformed as the deformation of the sheet 2. However, the shape of the main and the sub joint members is maintained when the occlusion pressure is released since the main and the sub joint members 9 are fixed by the sheet 2.

Figure 7:
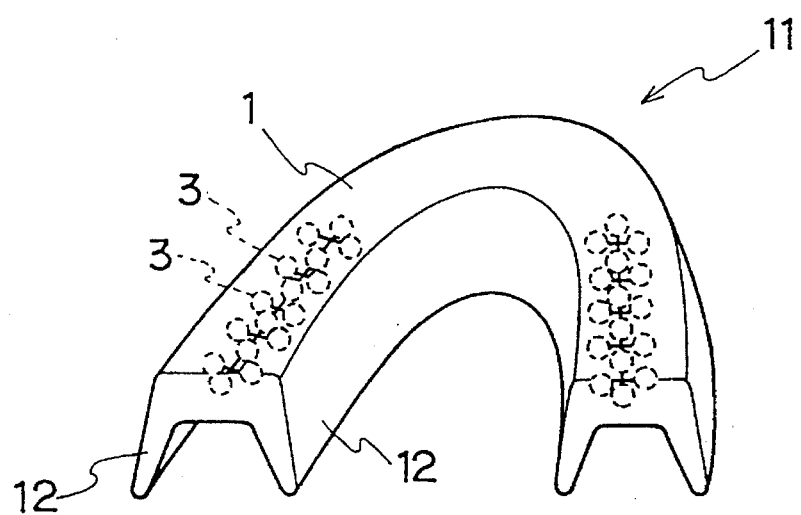
FIG. 7 is a perspective view illustrating an embodiment of a mouthpiece of the present invention.

FIG. 7 shows the mouthpiece 11 in which the spacer 1 is embedded. The spacer 1 for elevating position of occlusion which is embedded under the occlusion surface corresponding to the molars in the mouthpiece. Numeral 12 denotes a skirt extending in both sides of tongue and cheek. The mouthpiece 11 is formed into a horseshoe like shape which accords with dentition and made of thermoplastic elastomer such as ethylene-vinyl accetate copolymer. The mouthpiece 11 softened by soaking in hot water, thereafter the mouthpiece 11 is inserted into a mouth and bitten, at the same time the skirt 12 in the side of a tongue is pressed by the tongue, the skirt 12 in the side of lip and cheek is pressed by a finger, then the mouthpiece 11 is shaped. When the mouthpiece 11 is bitten, central occlusion is obtained if the mouthpiece is bitten in such a state as to draw in the chin. When the patient feels resistance, the patient stops to bite the mouthpiece 11, thereafter the elevation of occlusion position with a predetermined space is obtained. Hardness of the spacer 1 is preferably smaller so that the patient could not feel disorder when he bites it. It is preferable that the hardness of the spacer 1 by JIS-A is in a range from 40 to 90, and the hardness of the spacer 1 is set so as to be substantially the same as the mouthpiece 11. It is preferable that the spacer 1 is colored and mouthpiece 11 is transparent or semitransparent so that the elevation of occlusion position can be confirmed.

Figure 8:
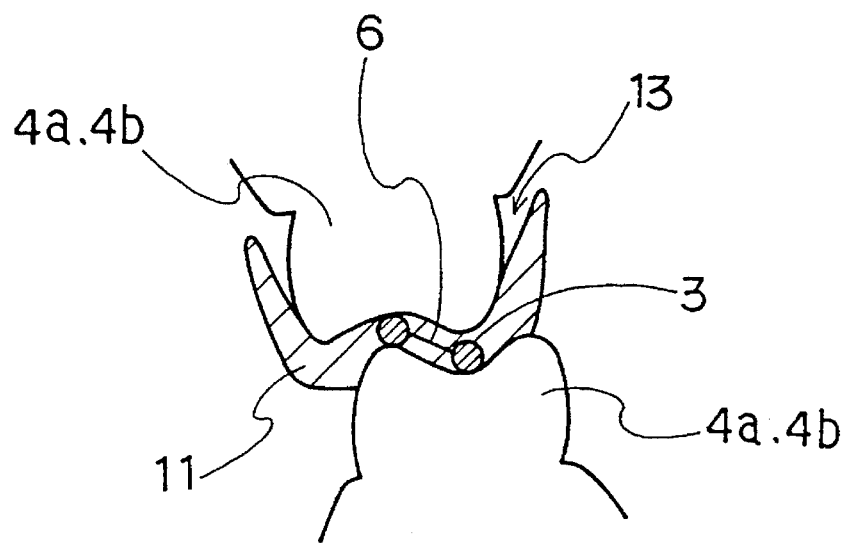
FIG. 8 is a sectional view showing a state wherein the mouthpiece is shaped.
Figure 9:
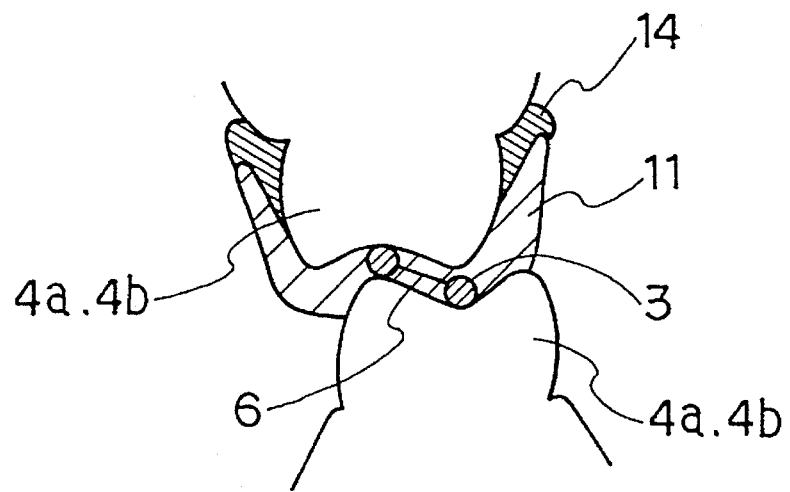
FIG. 9 is a sectional view showing a state wherein the mouthepiece as a personal tray.

With respect to the available mouthpiece and the mouthpiece in accordance with the above embodiment, it is very difficult to shape the skirt 12 in the mouth, and it often happens that an aperture 13 between the skirt 12 and the side face of molar 4a, 4b appears as shown in FIG. 8. The mouthpiece 11 having such an aperture 13 is not correctly mounted on the teeth, and is not enough to protect the teeth. Further, availability of the mouthpiece is very bad. When such mouthpiece 11 is used, the mouthpiece 11 is used as a personal tray as shown in FIG. 9, and the impressing material is charged in the mouthpiece, thereafter the mouthpiece is bitten by the player, then the accurate impression of the molars 4a, 4b is collected. When the mouthpiece is shaped on the basis of the impression, the mouthpiece having high accuracy can be produced.

Figure 10:
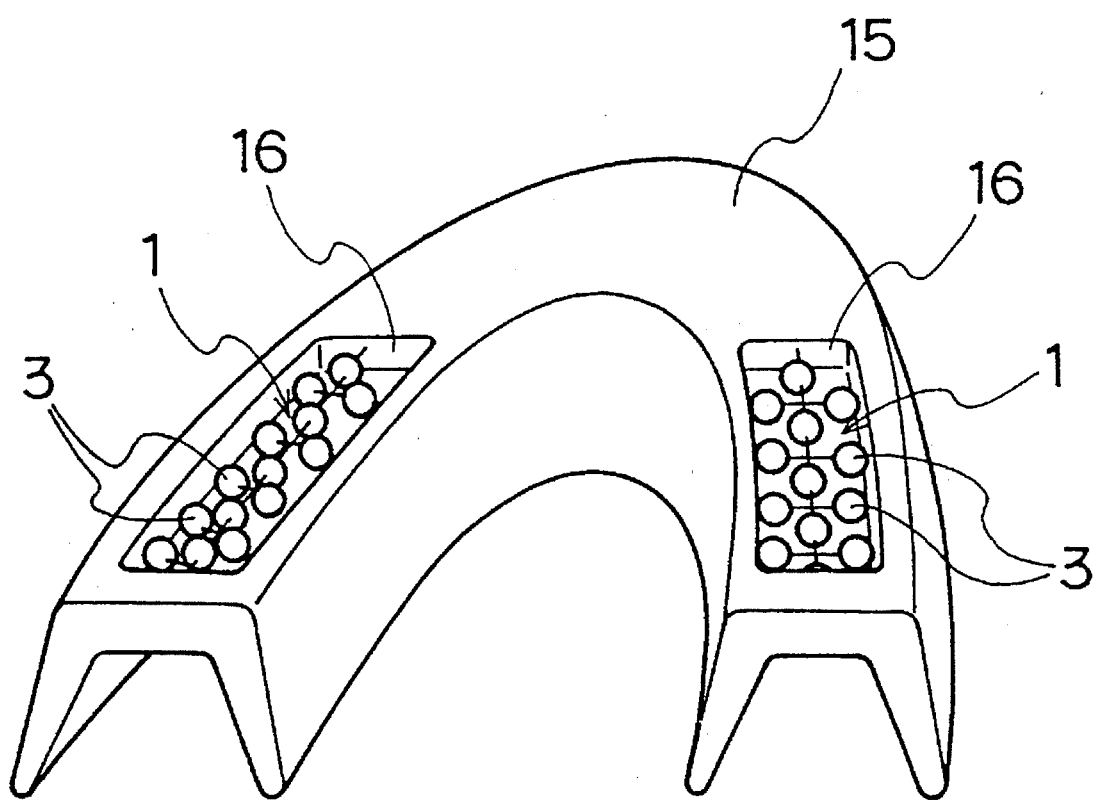
FIG. 10 is a perspective view of the personal tray which is provided with a spacer for elevating occlusion position.

FIG. 10 shows the construction of the mouthpiece wherein the ball members 3 are arranged in a groove 16 which is located in a portion corresponding to the molars and formed in the personal tray made of thermoplastic elastomer. A plurality of the ball members 3 is connected to each other by means of a string-like-shaped joint member, thereby the ball members 3 are arranged in the groove 16. The impressing material being made of plastic material is charged into the groove 16, thereafter the impressing material is inserted in the mouth and bitten. The upper and lower molars are positioned above the groove 16, the space between the upper and the lower molars is decided by the diameter of the ball member 3. In accordance with such method for shaping a mouthpiece, elevation of occlusion position can be accurately obtained with relatively low occlusion pressure since the impressing material has flowability in the initial state of shaping.

Figure 11:
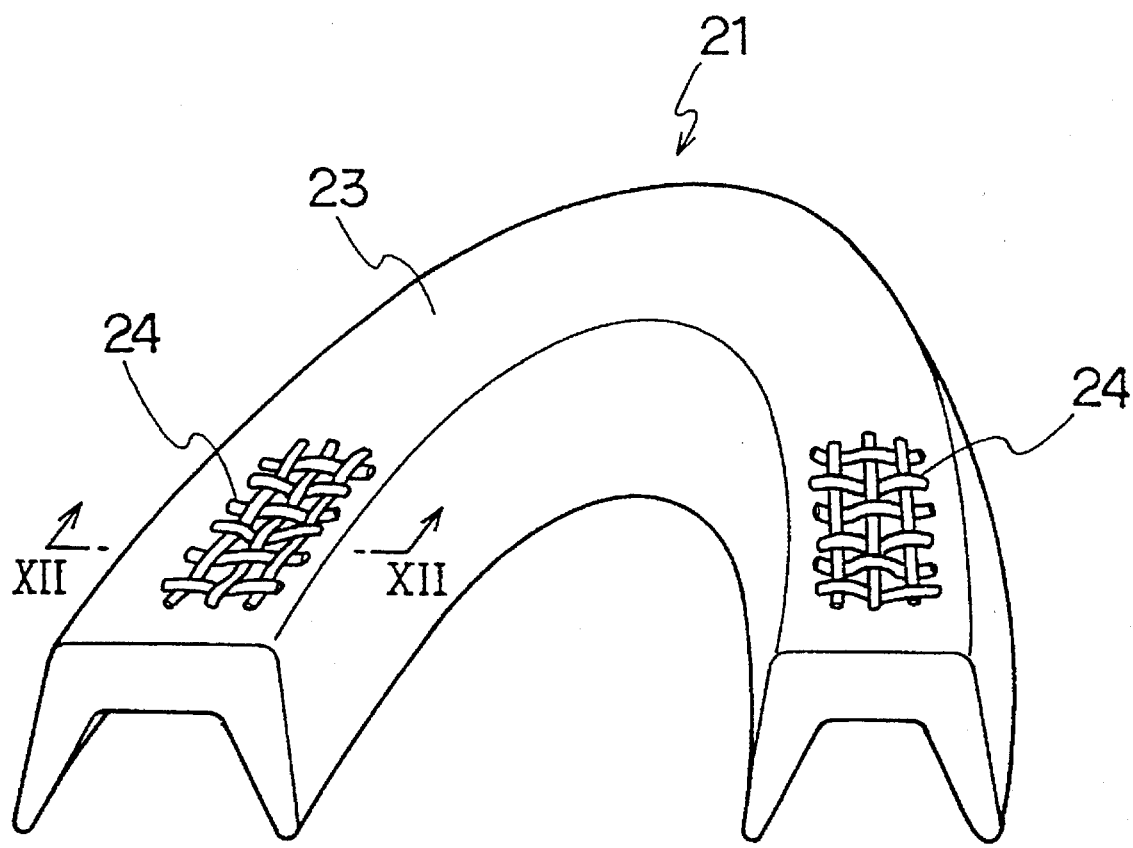
FIG. 11 is a perspective view showing yet another embodiment of a mouthpiece of the present invention.
Figure 12:
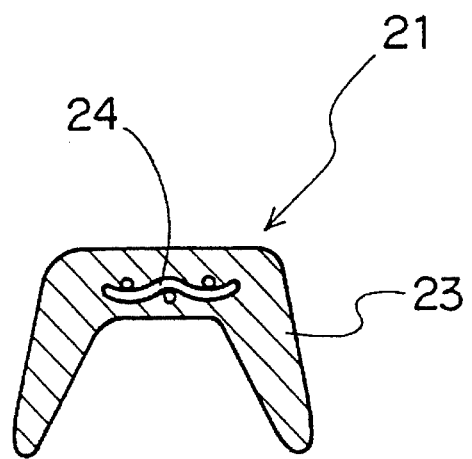
FIG. 12 is a sectional view along a line XII—XII in FIG. 11.
Figure 13:
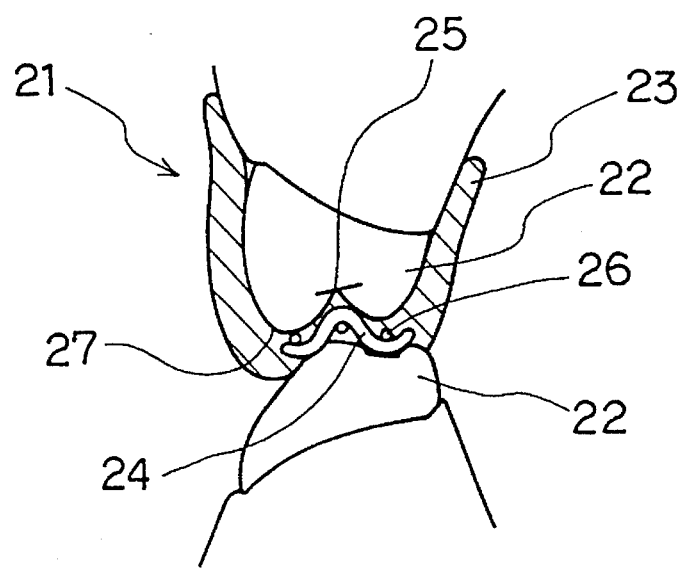
FIG. 13 is a sectional view showing a using state of the mouthpiece in FIG. 11.

In FIGS. 11 to 13, another embodiment of the mouthpiece 21 covering the teeth 22 on the upper jaw (or maxilla) is shown. The mouthpiece 21 comprises a mouthpiece body 23 and an elevating member 24 for elevating an occlusion position being embedded at a portion corresponding to the molars in the body 23. The mouthpiece body 23 is made of thermoplastic elastomer having a softening point being in a range from 50° to 100° C. such as the above-mentioned ethylene-vinyl acetate copolymer resin, formed into a horseshoe like shape corresponding with dentition, and provided with a skirt extending in the sides of a tongue, a cheek and a lip. The elevating member 24 has a softening point which is higher than 100° C. and a hardness which is substantially the same as that of the mouthpiece at the body temperature (37° C.). The hardness of both the elevating member 24 and the mouthpiece body 23 are in a range from about 40 to 90, and preferably they are in a range from 60° to 80° C.

As a material of the elevating member 24, the material having the above property such as thermoplastic elastomer (e.g. styrene block copolymer), chlorosulfonated polyethylene, polyolefin chloride is used with a flocculent state in the shape of a fiber. The fiber may be a filament, or twisting yarn of fine fibers. Diameter of the fiber is designed so as to accord with the elevation. The fibers may be woven to be a woven textile (including knitted goods). In this case, when diameter of the fiber is 1 mm, length of a portion wherein the fibers are crossed is 2 mm. The length is a value of elevation. With respect to the woven textile, spacing between a warp and a weft is preferably in a range from 1 to 2 mm, thereby the fiber can be located in the fossa 25 of the center of teeth 22, in the side of tongue of cuspis 26 and in the side of the cheek of the cuspis 27 as shown in FIG. 13.

Figure 14:
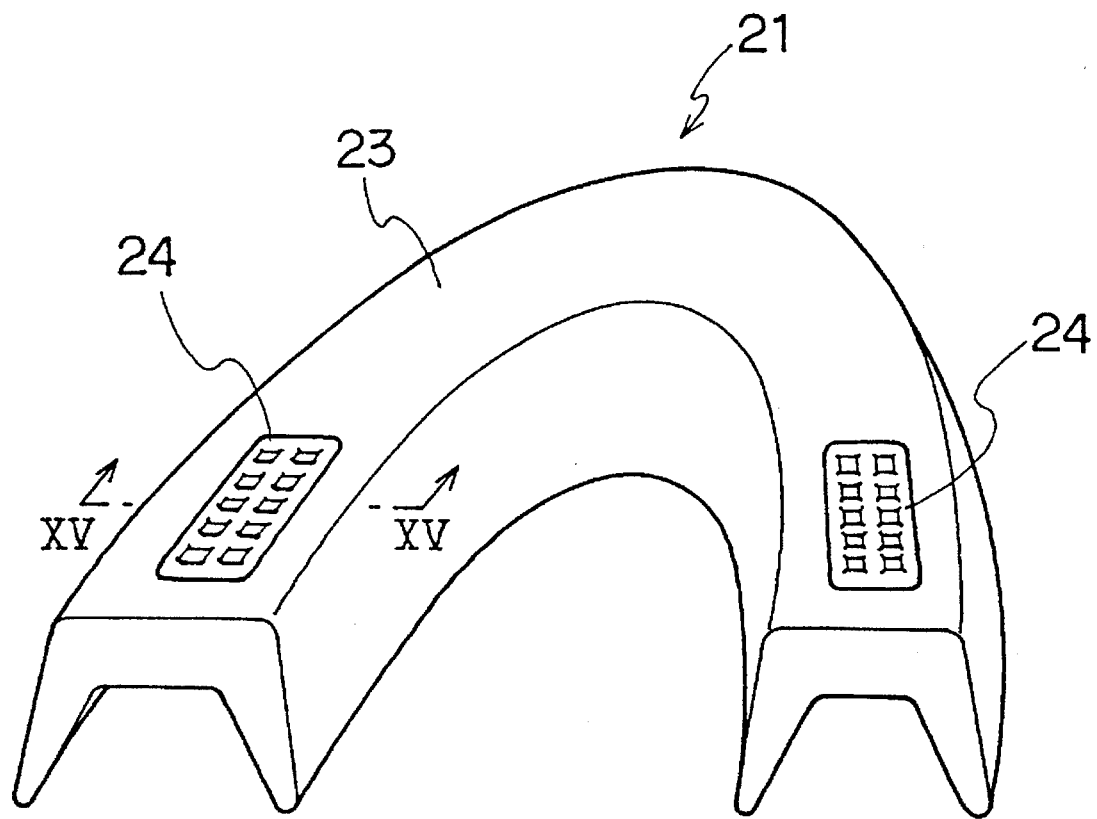
FIG. 14 is a perspective view showing yet another embodiment of a mouthpiece of the present invention.
Figure 15:
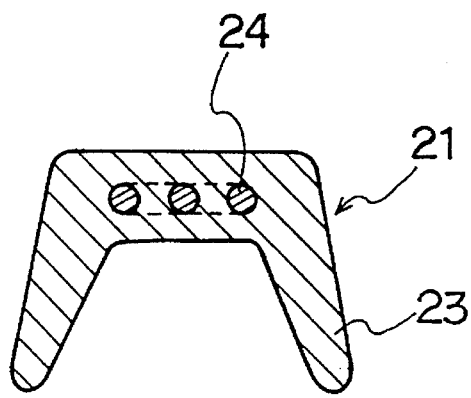
FIG. 15 is a sectional view along a line XV—XV in FIG. 14.
Figure 16:
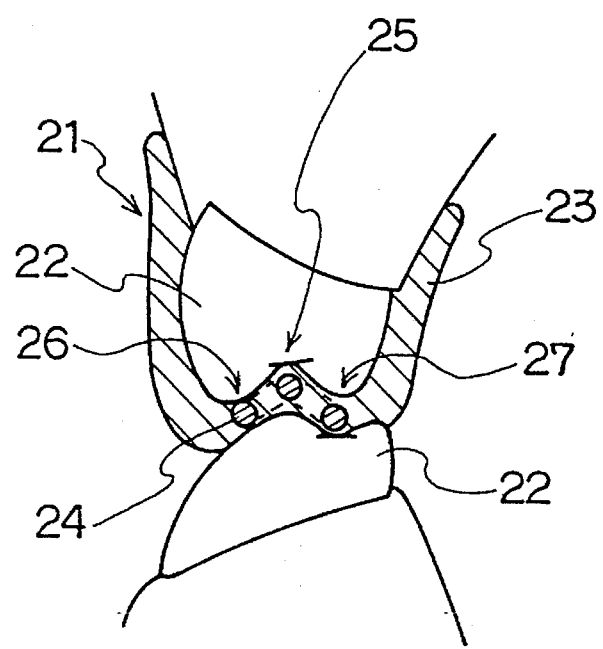
FIG. 16 is a sectional view showing a using state of the mouthpiece in FIG. 14.

In FIGS. 14 to 16, still another embodiment of the mouthpiece wherein a reticulate member is used as the elevating member 24. The above reticulate member is obtained by the string like member, each of which is connected. This type of the elevating member 24 can be integally formed by means of injection molding or the like using a material which is the same as the above embodiment. Even in the embodiment, the spacing between latticed lines is preferably in a range from about 1 to 2 mm, diameter of the line is designed so as to accord with the value (e.g. 2 mm) of elevation. Besides, portions except for the portion, wherein the lines in the reticulate member are crossed, are formed so as to be thin, thereby the reticulate member is easily deformed as a whole, and a restoring force can be canceled when the occlusion pressure is released.

As the material of the elevating member 24, when RABALON (trademark of MITSUBISHI PETROCHEMICAL COMPANY, LTD.), which is styrene block copolymer, is used, softening point of the elevating member 24 is about 130° C. For this reason, the elevating member is not softened in hot water at 100° C., but in such a state as to be deformable. Accordingly, when the elevating member 24 is interposed between the upper and the lower teeth in the mouth, and applied to an occlusion pressure, the elevating member 24 is deformed along the occlusion plane due to the occlusion pressure. However, the elevating member is not depressed so that the predetermined value of elevation can be obtained.

The value of elevation of the mouthpiece 21 for an athelete may be in a range from about 1.0 to 3.0 mm, and the standard value is about 2.0 min. With respect to the mouthpiece used for curing axis deviation of upper and lower jaw and the like, the value of elevation is designed so as to be approximately in a range from 0.3 to 6.0 mm. When the elevation is subjected in producing an artificial denture, the value of elevation is often set at a value being in a range from 0.5 to 1.0 min.

The mouthpiece 21 wherein the elevating member 24 is embedded is soaked in hot water for about 10 sec, the upper teeth are covered with the softened mouthpiece, thereafter the mouthpiece pressed from the inside thereof by the tongue, and from the outside (the side of the cheek and the lip) thereof by the finger, thereby the mouthpiece is shaped so as to be closely contacted with the teeth. Then, the elevating member 24 is deformed to a force of occlusion, the fiber is positioned at fossa 25 of the tooth, the cuspis 26 of the side of the tongue and the cuspis 27 of the side of the cheek. Besides, the elevating member 24 can be practically used if the elevating member 24 is disposed so as to correspond with the fifth and the sixth molars.

In accordance with the spacer for elevating occlusion position of the present invention, the elevation of occlusion position is subjected by arranging the ball members having a predetermined diameter in a plane, embedding the ball members in the sheet being made of plastic material, thereby the elevations can be subjected with an accurate space. Further, the spacer wherein a plurality of ball members are connected by the joint members and the ball members are embedded in the sheet made of the plastic material enable to elevate occlusion position so as to correspond with the diameter of the ball member since each of the ball members is placed one above the other.

Further, in accordance with the mouthpiece of the present invention, the elevation of occlusion position can be subjected so as to accord with the design value, thereby shock can be effectively relieved or absorbed.

Furthermore, when the teeth are covered with the mouthpiece to shape by a user, if the user stops to bite the mouthpiece at the position wherein the user feels resistance, elevation of occlusion position can be obtained so as to correspond with the elevation (design value). For this reason, the effect of relieving a shock can be performed by the mouthpiece most efficiently.

Besides, in accordance with the present invention, occlusion portion is spaced by the elevating member, thereby this portion does not become thin abnormally, or is not bitten off. For this reason, durability of the mouthpie can be improved.

What we claim is:

1. A mouthpiece comprising a mouthpiece body being made of a thermoplastic elastomer having a softening point which is in a range of 50° to 100° C.; and an elevating member for elevating occlusion position with a predetermined space; said mouthpiece body being formed into a horseshoe shape so as to accord with dentition having an arc shape;

said elevating member having a softening point which is higher than 100° C., and being made of a string member having a hardness which is substantially the same as that of said mouthpiece body at a temperature of 37° C., wherein said elevating member is located in a position corresponding only to the fifth and sixth teeth, said elevating member being distorted due to a distortion of the mouthpiece body in accordance with an occlusion surface when upper and lower teeth are bitten.

2. A mouthpiece of claim 1 wherein said string like member is a fiber.

3. A mouthpiece of claim 2 wherein said elevating member is a woven textile made of said fiber.

4. A mouthpiece of claim 1 wherein said elevating member further comprises a reticulate member which is connected with said string member.

5. A mouthpiece comprising a mouthpiece body being made of a thermoplastic elastomer having a softening point which is in a range of 50° to 100° C.; and an elevating member for elevating occlusion position with a predetermined space; said mouthpiece body being formed into a horseshoe shape so as to accord with dentition having an arc shape;

said elevating member having a softening point which is higher than 100° C., and being made of a string member forming latticed lines having a hardness which is substantially the same as that of said mouthpiece body at a temperature of 37° C., wherein the spacing between the latticed lines of the string member is in the range from about 1 to 2 mm and said elevating member is located in a position corresponding only to the fifth and sixth teeth.

* * * * *